United States Patent [19]

Schönhöffer

[11] Patent Number: 6,015,436
[45] Date of Patent: Jan. 18, 2000

[54] IMPLANT FOR FILLING A SPACE BETWEEN VERTEBRAE

[75] Inventor: Helmut Schönhöffer, Ulm, Germany

[73] Assignee: Heinrich Ulrich, Ulm/Donau, Germany

[21] Appl. No.: 09/011,418

[22] PCT Filed: May 22, 1997

[86] PCT No.: PCT/DE97/01065

§ 371 Date: Apr. 17, 1998

§ 102(e) Date: Apr. 17, 1998

[87] PCT Pub. No.: WO97/47258

PCT Pub. Date: Dec. 18, 1997

[30] Foreign Application Priority Data

Jun. 7, 1996 [DE] Germany ............................ 196 22 827

[51] Int. Cl.⁷ ................................. A61F 2/02; A61F 2/28; A61F 2/44
[52] U.S. Cl. ................................................ 623/17; 623/16
[58] Field of Search ................................. 623/17, 16, 11; 606/73

[56] References Cited

U.S. PATENT DOCUMENTS 5,336,223  8/1994  Rogers ........................................ 606/61
5,358,524 10/1994  Richelsoph ................................ 623/16
5,702,455 12/1997  Saggar ....................................... 623/17

FOREIGN PATENT DOCUMENTS 2666221   3/1992  France ........................................ 623/16
19509317  9/1996  Germany .................................... 623/17

*Primary Examiner*—Mickey Yu
*Assistant Examiner*—Alvin Stewart
*Attorney, Agent, or Firm*—Herbert Dubno

[57] ABSTRACT

The implant includes of two end implant parts (1, 2) for positioning on the adjacent vertebrae and a center implant part (3) arranged therebetween, which is connected by a thread (4) with one of the end implant parts, whereby by turning the center implant part (3) the length of the implant can be altogether changed. The end implant parts (1, 2) form tubular sleeves (5', 5") with sleeve walls perforated by openings (6) and interengage axially with their sleeves (5', 5"), whereby they are guided on the sleeve walls to be axially slidable with respect to each other, as well as secured against mutual pivoting about the sleeve axis. The thread (4) is provided between the center implant part (3) and the end implant part (1) connected therewith by the thread and the center implant part (3) pivotable in the thread (4) is designed as an axial stop for the other end implant part (2).

6 Claims, 8 Drawing Sheets

IMPLANT FOR FILLING A SPACE BETWEEN VERTEBRAE

CROSS REFERENCE TO RELATED APPLICATIONS

This application is a national stage of PCT/DE97/01065 filed May 22, 1997 and based upon German national application 196 22 827.1 filed Jun. 7, 1996.

FIELD OF THE INVENTION

The invention relates to an implant for insertion between vertebral bodies as a replacement, consisting of two end implant parts to be positioned on the two adjacent vertebrae, and between them a center implant part which is connected by a thread to one of the end parts of the implant, whereby the three implant parts and the threading are arranged coaxially in the longitudinal direction of the spinal column and, by a rotation of the center implant part, the overall length of the implant can be adjusted and whereby end parts of the implant form tubular sleeves whose sleeve walls are perforated by openings.

BACKGROUND OF THE INVENTION

Implants of this kind are known from DE 44 23 527 A1 and serve as replacements for vertebrae or vertebral parts ablated from the spinal column. The implants make possible a distraction of the spinal column region containing the implant by twisting the center part of the implant. Each of the two end parts of the implant can be connected with the center implant part by its own screw thread, whereby the two threads are arranged coaxially in the longitudinal direction of the spinal column and run in opposite directions with respect to each other. If desired, through the openings in the implant parts it is possible to introduce a material to be put inside tubular elements, such as bone cement or bone fragments, to achieve a quicker attachment of the implant. Therefore the implant is well suited for the induction of bone formation and stimulation of bone growth and after implantation can grow easily and quickly into the bone. In any case in these implants the total axial length is at least equal to the total length of two oppositely working threads, which is a limitation of the minimal implant length, so that these known implants can not be used as intervertebral spacers or as intervertebral disk replacements.

OBJECT OF THE INVENTION

It is an object of the invention to provide an improved implant of the aforementioned kind, so that it can be adjusted to a minimal length, making possible its use not only as a complete replacement of a vertebral body, particularly in the area of the cervical vertebrae, but also as an intervertebral spacer for the replacement of an intervertebral disk, especially in the lumbar region.

SUMMARY OF THE INVENTION

According to the invention this object is attained in an implant in which the two end implant parts interengage axially with their sleeves and are guided at the sleeve walls axially slidably with respect to each other, and are secured against mutual pivoting about the sleeve axis. The thread between the center implant part and the end part which is connected therewith by the thread is provided on its sleeve. The center implant which can be rotated in the thread of this sleeve and is designed as an axial stop for the other end part of the implant.

Since the implant of the invention has only one screw thread the minimal length to which the implant can be shortened is determined only by the length of this single thread, since the two end parts of the implant can be practically completely threaded into each other over the entire length of their tubular sleeves, which altogether results in an axially very low construction, thereby making possible the use of the implant as a replacement for intervertebral disks. Nevertheless the distraction capability of the implant during surgery is fully maintained, since only the center implant part has to be correspondingly pivoted in the thread for the desired length of the implant to be set.

An embodiment of the implant of the invention, which is particularly simple and advantageous from the manufacturing, assembly and handling point of view, has the sleeve of the end implant part connected by the screw thread to the center implant part with its thread on its outer periphery, and is radially surrounded on the outside by the center implant part as well as by the sleeve of the other end part of the implant. In this way the center implant part is easily accessible for turning and the thread of the end implant part guiding the center part of the implant is axially overridden on the outside by the sleeve of the other end implant part.

It is also advantageous to secure the two end implant parts against mutual pivoting, so that in the sleeve wall of one of this implant parts and an axially running guide slot is provided, while on the sleeve wall of the other implant part a guide projection engaging in this slot is provided. Several guide slots and guide projections can be distributed over the periphery of the sleeve walls.

In order to be able to fix the mutual position of the two end implant parts also independently of the stopping function of the center implant part, a further advantageous embodiment of the invention has, in the area where the sleeves of both end implant parts overlap, in at least one radial threaded bore, the sleeve of one of the end implant parts, wherein a clamping screw is guided, which can be braced against the sleeve of the other end implant part.

In a further preferred embodiment one or both end implant parts can be provided at the respective end facing away from the center implant part with an annular front plate and this front plate can be provided with cutting edges or points for penetrating the adjacent vertebra.

Within the framework of the invention there is a certain freedom of choice regarding the configuration and arrangement of the openings in the sleeve walls of the end implant parts. On the one hand the total cross section clearance represented by the openings is supposed to be as big as possible, on the other hand the openings are not allowed to unacceptably weaken the thread area, so that the strength of the thread connection between the one end implant part and the center implant part connected therewith is not impaired. Generally the openings are shaped like bores with a circular cross section or like elongated holes and are uniformly distributed over the sleeve periphery. Advantageously further openings are arranged in the outer peripheral surface of the center implant part, distributed over its periphery, and are shaped like keyhole openings for the insertion of a key serving for turning the center implant part.

BRIEF DESCRIPTION OF THE DRAWING

The above and other objects, features, and advantages will become more readily apparent from the following description, reference being made to the accompanying drawing in which.

SPECIFIC DESCRIPTION

Figure 1:
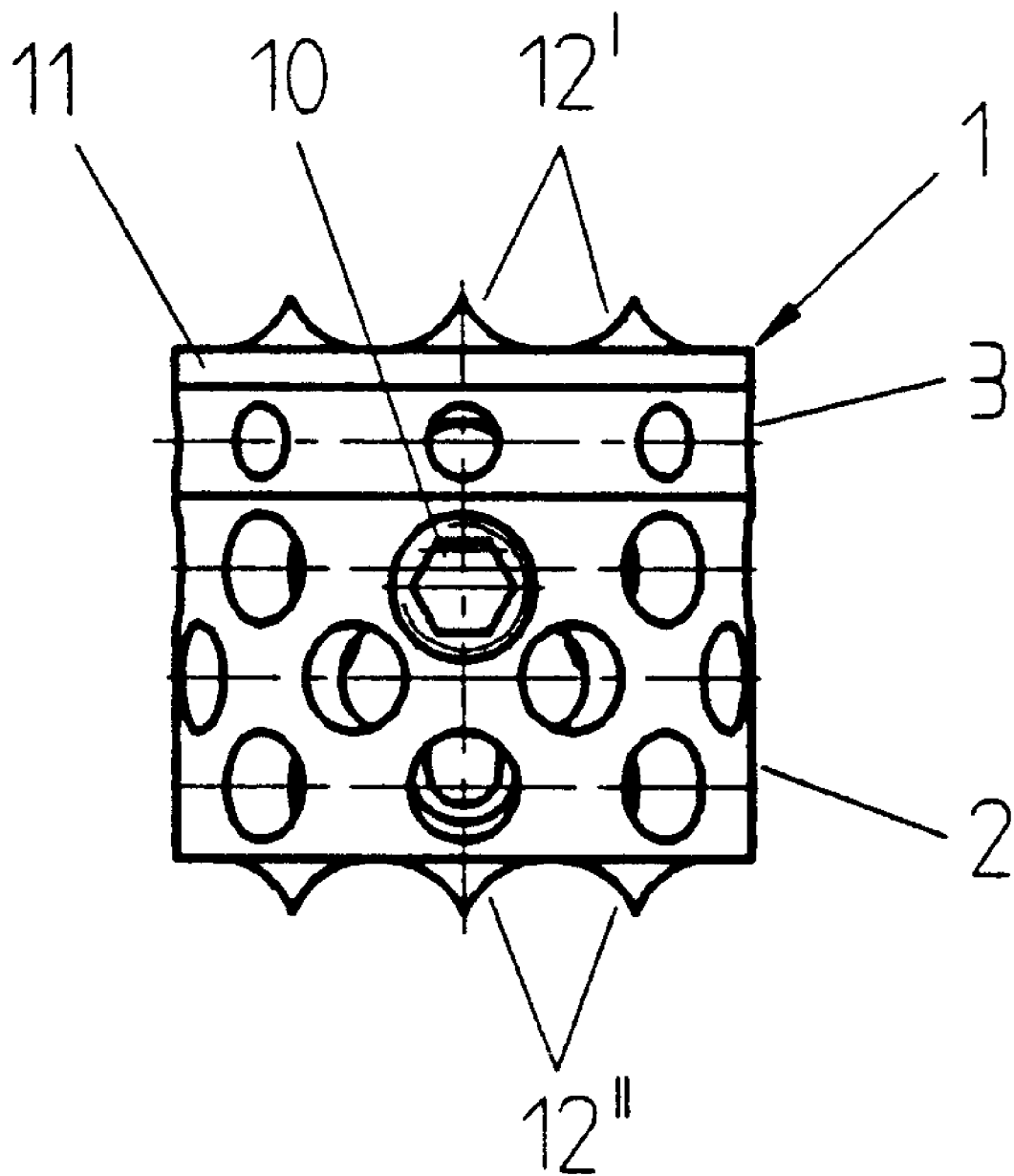
FIG. 1 is a side view of an implant according to the invention in a position wherein the implant is set to its possible minimal length.

The implant represented in the drawing serves for the insertion between vertebrae not shown in the drawing as a replacement, namely depending on the length setting of the implant, as a replacement of an intervertebral disk or of vertebrae or vertebral parts ablated from the spinal column. The implant consists of two end implant parts 1 and 2 for the contact with the respective adjacent vertebrae and a center implant part 3 located between them. The center implant part 3 is connected by means of a thread 4 with one of the two end implant parts, respectively in the drawing with upper end implant part 1.

Figure 2:
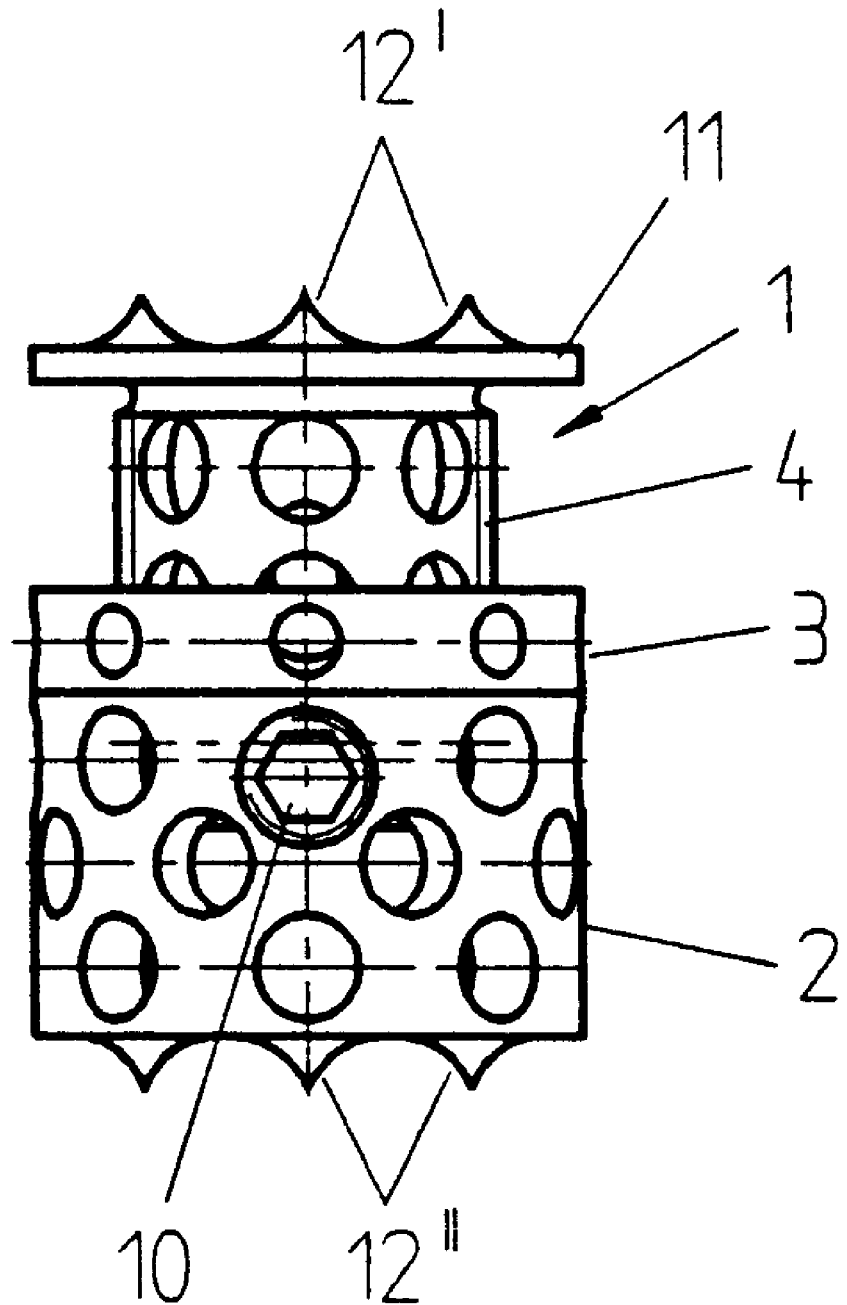
FIG. 2 is a view similar to FIG. 1 but in a position wherein the implant is set to its possible maximal length.
Figure 3:
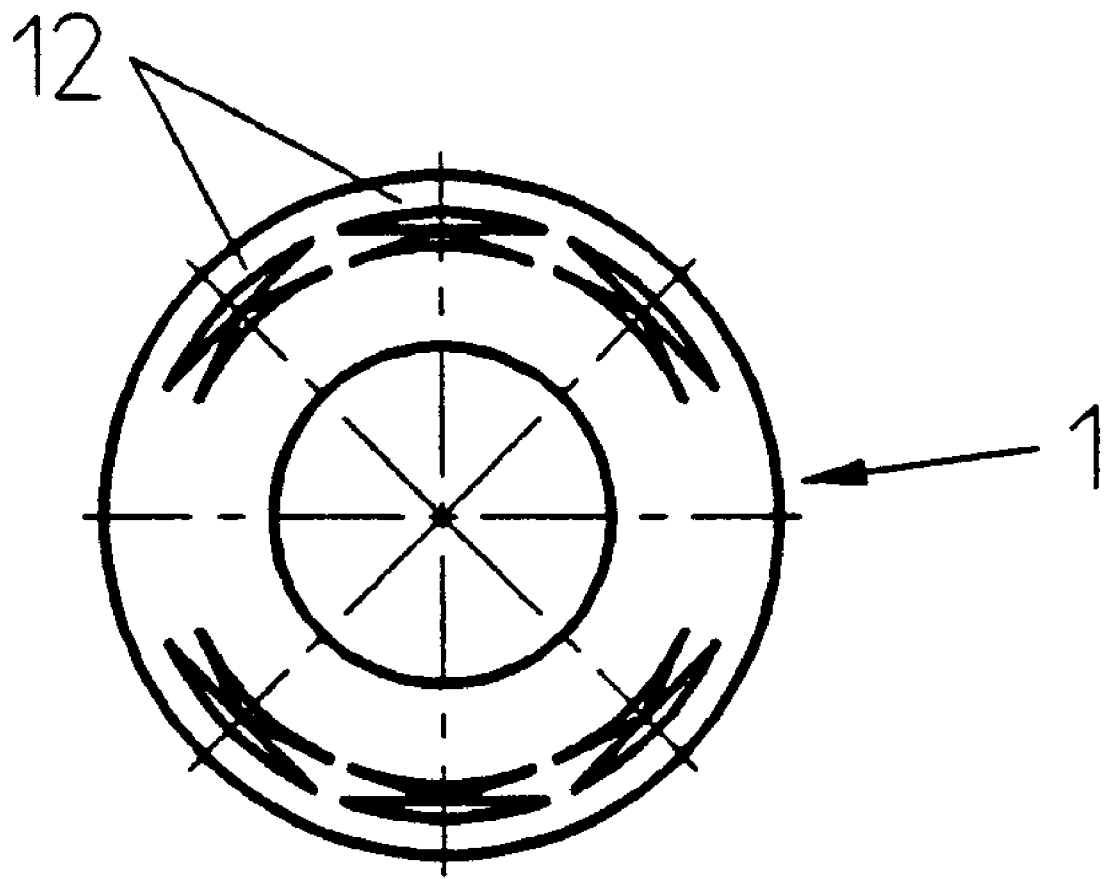
FIG. 3 is an end view of the implant.
Figure 4:
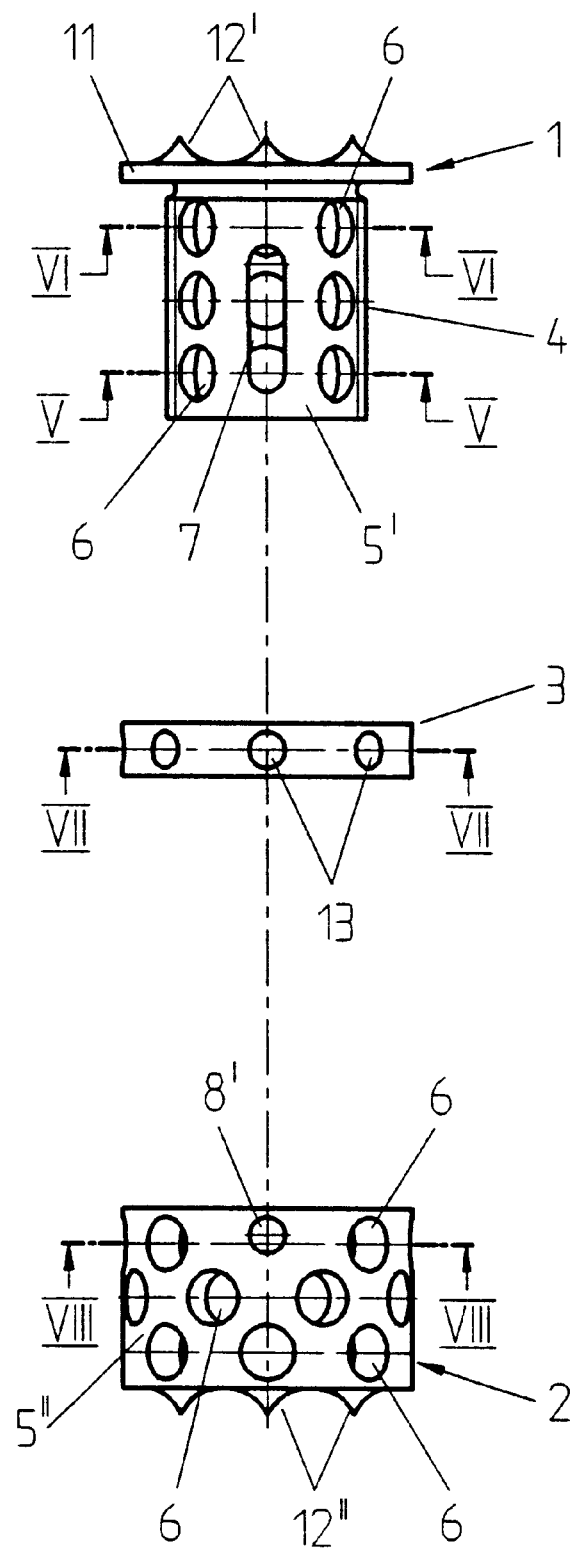
FIG. 4 is an exploded view of the implant according to FIG. 1 and 2.
Figure 5:
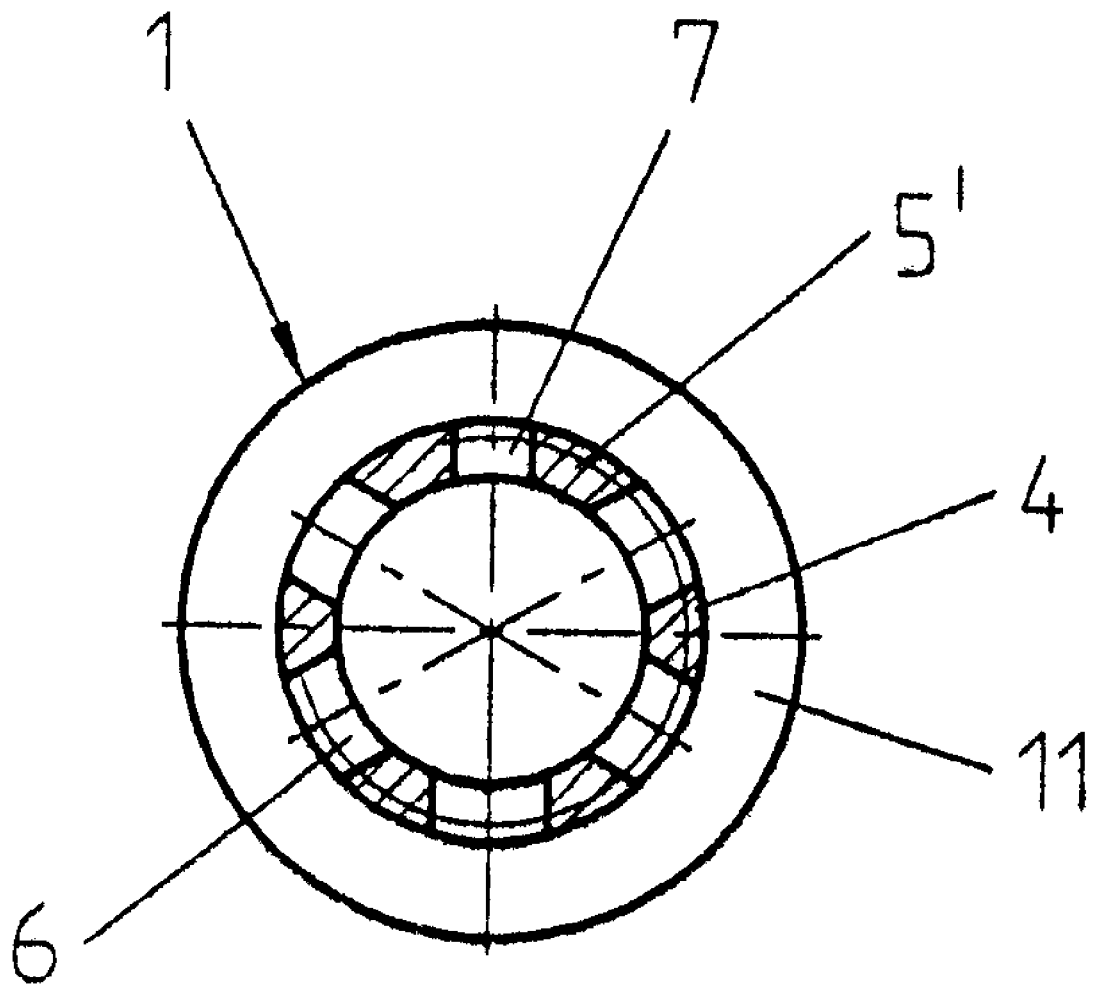
FIG. 5 is a section along the line V—V in FIG. 4.
Figure 6:
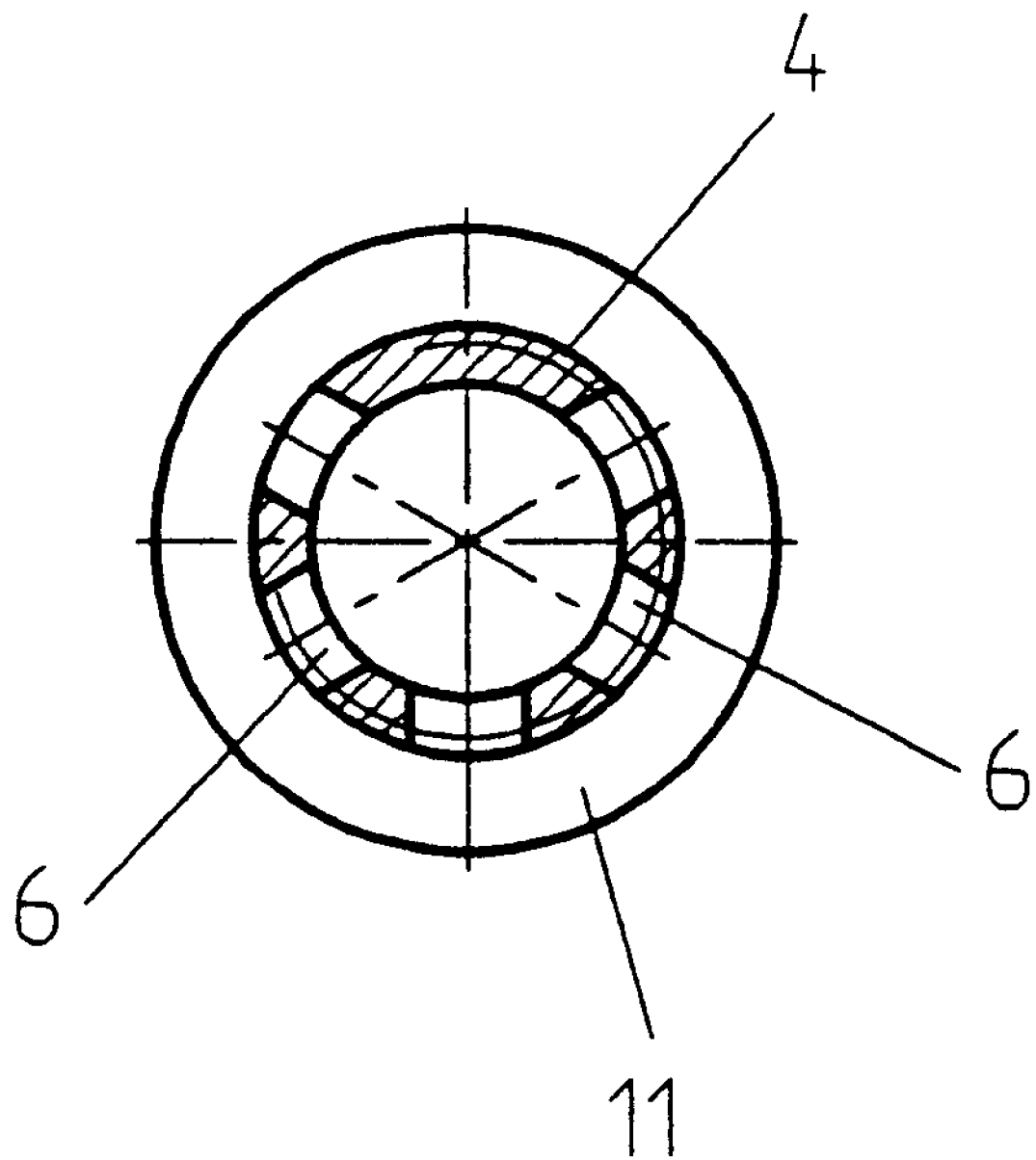
FIG. 6 is a section along the line VI—VI in FIG. 4.
Figure 7:
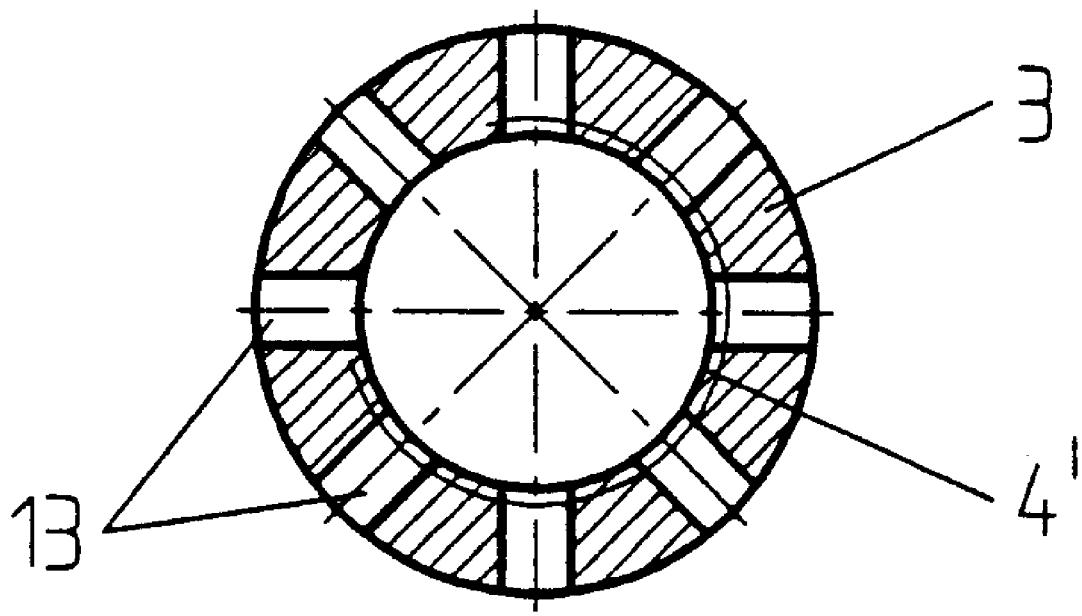
FIG. 7 is a section along the line VII—VII in FIG. 4.
Figure 8:
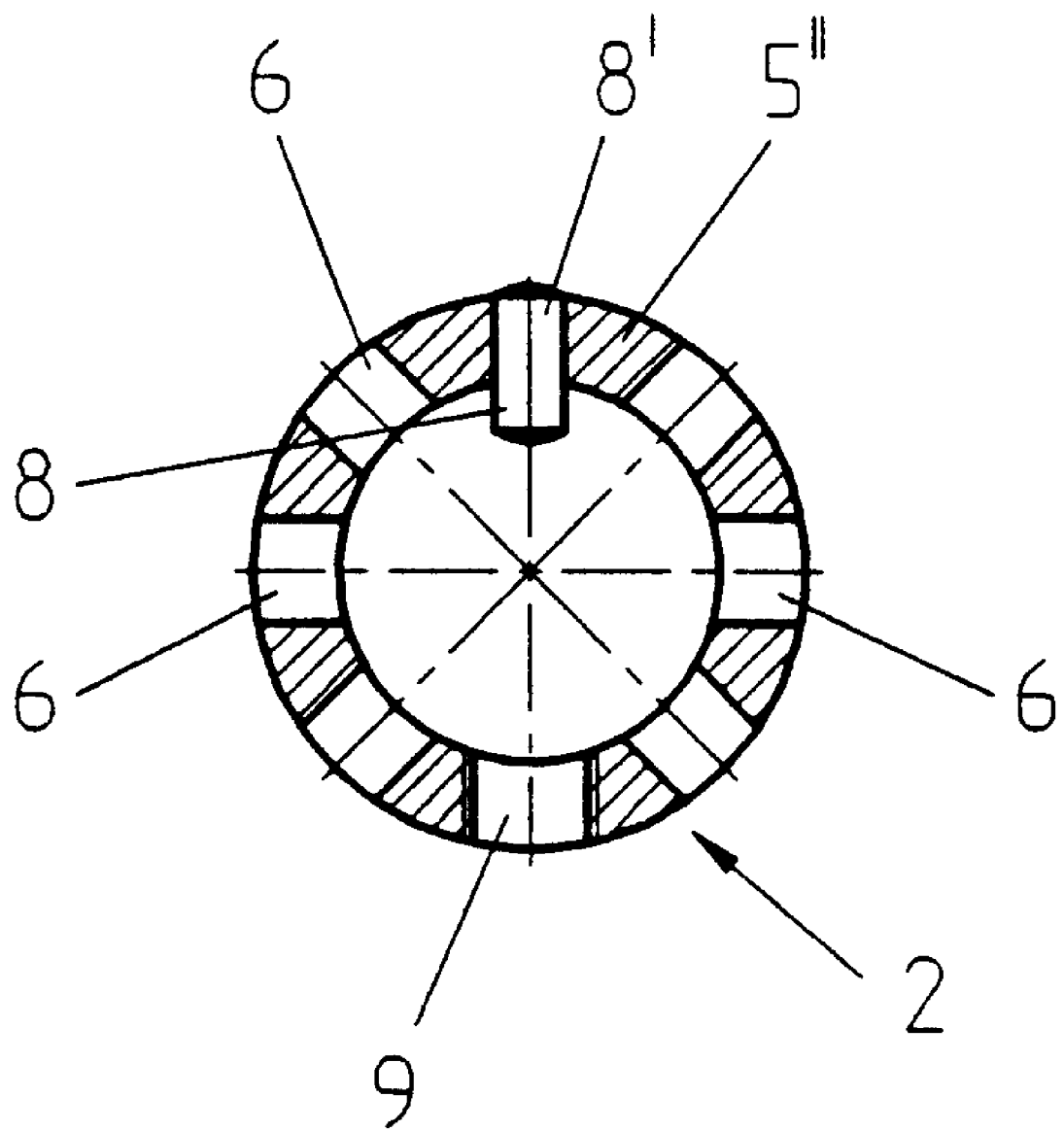
FIG. 8 is a section along the line VIII—VIII in FIG. 4.

The three implant parts 1 to 3 and the thread 4 are arranged coaxially in the longitudinal direction of the spinal column. By turning the center implant part 3 in the thread 4 the length of the implant can be changed with the limits visible from the comparison of FIG. 1 and 2. The end implant parts 1 and 2 (inner and outer parts, respectively,) form tubular sleeves 5', 5" with sleeve walls perforated by openings 6, whereby the openings 6 make possible a rapid growth of the implant into the surrounding tissue. The two end implant parts 1 and 2 engage axially into each other with their sleeves 5', 5". They are guided at the sleeve walls in an axially slidable manner, as well as secured against mutual pivoting about the sleeve axis in a manner which is still to be explained.

The thread 4 between the center implant part 3 and the end implant part connected to it by threading, i.e. in the drawing the upper end implant part 1, is arranged on its sleeve 5'. The center implant part 3 pivotable in the thread 4 of this sleeve 5' is designed as an axial stop for the sleeve 5" of the other, in the drawing the lower end implant part 2, i.e. directly abuts the end of the latter. By turning the center implant part 3 in the screw thread 4 of the upper end implant part 1, the axial position of the center implant part 3 on the upper end implant part 1 changes, so that the relative position of the two end part implants 1 and 2 also changes, since the position of the end implant part 2 shown as the lower one in the drawing with respect to the end implant part 1 shown in the upper part of the drawing is determined by the arrest of its sleeve 5" on the center implant part 3.

The sleeve of the upper end implant part 1 bears the thread 4 on its outer peripheral surface. The center implant part 3 radially surrounding the sleeve 5' on the outside engages in this thread 4 with a female thread 4'. The sleeve 5' of the end implant part 1 shown in the upper part of the drawing, which is connected by the thread to the center implant part 3, is also radially surrounded on the outside by the sleeve 5" of the other end implant part 2.

In order to secure the two end implant parts 1, 2 against mutual pivoting, in the sleeve wall of the end implant part 1 shown in the upper part of the drawing an axially running guide slot 7 is provided, while on the sleeve wall of the other end implant part 2 shown in the lower part of the drawing a guide projection 8 is provided. The guide projection 8 is formed by a pin 8' radially imbedded in the sleeve wall. With its length the guide slot 7 determines the extent of the mutual axial displacement of the two end implant parts 1, 2. Further the sleeve 5" of the lower end implant part 2 has at least one radial threaded bore 9 in the area where it overlaps with the sleeve 5' of the upper end implant part 1, wherein a clamping screw 10 braceable against the sleeve 5' of the upper end implant part 1 is guided, so that when the clamping screw 10 is tightened, the two end implant parts 1, 2 cannot be pulled apart axially. Further the upper end implant part 1 is provided at its end facing away from the center implant part 3 with an annular front plate 11 protruding radially towards the outside over the thread diameter, which is provided at its frontal surface with cutting edges or points 12' for penetrating the adjacent vertebrae. Corresponding cutting edges or points 12" are located on the axially opposite frontal sleeve rim of the lower end implant part 2. The center implant part 3 is provided on its outer peripheral surface with openings 13 distributed over the periphery, which are shaped like keyhole openings for the insertion of a key not shown in the drawing, which serves for turning the center implant part 3.

I claim:

1. A spinal implant selectively insertable as a vertebral replacement and as an insert between vertebrae, said implant comprising:

an inner implant part having a tubular perforated sleeve and formed with a screw thread;

an outer implant part having a tubular perforated sleeve and receiving said sleeve of said inner implant part, said sleeve of said inner implant part being axially slidable in said sleeve of said outer implant part;

a center implant part braced on an end of said outer implant part and threadedly engaged with the screw thread on said sleeve of said inner implant part for altering a length of said implant, said parts and said screw thread being coaxial; and means for preventing relative rotation of said inner and outer implant parts about a common axis of said sleeves.

2. The spinal implant defined in claim 1 wherein said sleeve of said inner implant part is formed with said screw thread along its external periphery and is surrounded by said center implant part and by the sleeve of said outer implant part.

3. The spinal implant defined in claim 1 wherein said means for preventing relative rotation of said inner and outer implant parts about said common axis of said sleeve includes an axially-extendable slot in one of said inner and outer implant parts, a guide projection on the other of said inner and outer implant parts engaged in said slot.

4. The spinal implant defined in claim 1 wherein one of said sleeves has a radial threaded bore receiving a screw braced against the other of said sleeves.

5. The spinal implant defined in claim 1 wherein one of said inner and outer implant parts is provided at an end turned away from the center implant part with an annular front plate provided with means for penetrating into an adjacent vertebrae.

6. The spinal implant defined in claim 1 wherein said center implant part is provided with openings distributed over a periphery thereof for receiving a key for turning the center implant part.

* * * * *